United States Patent [19]

Wierzbicki et al.

[11] Patent Number: 5,266,718
[45] Date of Patent: Nov. 30, 1993

[54] ETHANOLAMINE BENZOATE COMPOUNDS

[75] Inventors: Michel Wierzbicki, L'Etang la Ville; Pierre Hugon, Rueil Malmaison; Jacques Duhault, Croissy sur Seine; Francoise Lacour, Vincennes; Michelle Boulanger, Marly le Roi, all of France

[73] Assignee: Adir et Compagnie, Courbevoie, France

[21] Appl. No.: 898,916

[22] Filed: Jun. 12, 1992

Related U.S. Application Data

[63] Continuation-in-part of Ser. No. 883,207, May 14, 1992, abandoned.

[30] Foreign Application Priority Data

Jun. 14, 1991 [FR] France ............... 91 07289

[51] Int. Cl.$^5$ ........................... C07C 101/34
[52] U.S. Cl. ........................... 560/36; 560/37; 560/106
[58] Field of Search ............ 560/106, 36, 37; 514/513, 530, 540

[56] References Cited

U.S. PATENT DOCUMENTS

| | | | |
|---|---|---|---|
| 4,136,197 | 1/1979 | Hübner et al. | 424/319 |
| 4,237,165 | 12/1980 | Duhault | 424/308 |
| 4,603,145 | 7/1986 | Devries et al. | 514/539 |

FOREIGN PATENT DOCUMENTS 6608794 12/1966 Netherlands .

Primary Examiner—José G. Dees
Assistant Examiner—Samuel Barts
Attorney, Agent, or Firm—Gordon W. Hueschen

[57] ABSTRACT

New ethanolamine benzoate compounds which can be used as medicaments and correspond to the formula:

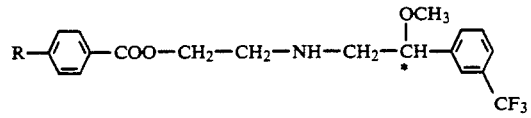

wherein R is as defined in the description, in the form of racemic compounds and enantiomers. These new compounds and their physiologically tolerable salts can be used therapeutically for treatment of insulin-resistance states.

10 Claims, No Drawings

ETHANOLAMINE BENZOATE COMPOUNDS

The present application is a continuation-in-part of our prior-filed co-pending application Ser. No. 07/883,207 filed May 14, 1992, now abandoned.

The present invention relates to new ethanolamine benzoate compounds, a process for their preparation and pharmaceutical compositions containing them.

It relates especially to ethanolamine benzoate compounds of formula I:

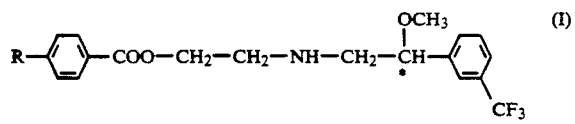

wherein:
R represents:
a hydrogen atom, or
a group of formula:

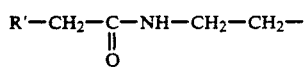

wherein R' represents:
a) either a radical of formula:

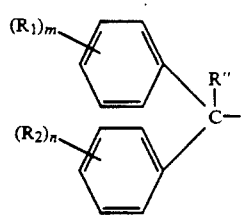

wherein:
R" represents a hydrogen atom or a straight-chain or branched alkyl radical containing from 1 to 5 carbon atoms,
$R_1$ and $R_2$, which are the same or different, each represents a hydrogen atom or a straight-chain or branched alkyl or alkoxy radical each having from 1 to 5 carbon atoms, and m and n are the same or different and each represents 1, 2 or 3;
b) or a fluorenyl radical of formula:

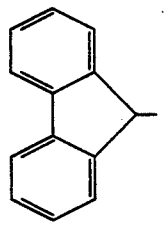

in the form of a racemic compound or in the form of enantiomers.

The prior art is illustrated especially:
by French Patents 1 517 587 and 6564 M which respectively relate to:
compounds of formula:

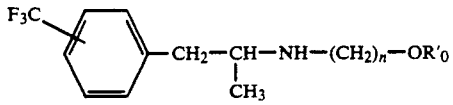

wherein:
n represents, inter alia, the value 2, and
$R'_0$ represents a hydrogen atom or a group $COR''_0$, $R''_0$ being, inter alia, an optionally substituted phenyl radical, and
the use of these compounds as medicaments in the treatment in particular of obesity, pain and epilepsy; and
by U.S. Pat. No. 4,237,165, which relates to pharmaceutical compositions comprising either 1-(3-trifluoromethylphenyl)-2-($\beta$-hydroxyethyl)aminopropane or 1-(3-trifluoromethylphenyl)-2-($\beta$-benzoyloxyethyl)aminopropane, which can be used in the treatment of disorders of the metabolism.

Substantial structural modifications have resulted in the compounds of formula I of the present invention, which regulate the metabolism of glucides and lipids and counter the oxidation of LDLs but have no effect on the level of cerebral serotonin, which is not true of the compounds of the prior art mentioned above which are inactive with respect to the oxidation of LDLs and do modify the level of cerebral serotonin, as demonstrated by the pharmacological study described in Example 10.

The present invention also relates to a process for the preparation of compounds of formula I which is characterised in that:
the acid of formula II:

wherein R has the meaning given hereinbefore, is converted into a salt of formula II':

wherein R has the meaning given hereinbefore and M is an alkali metal or alkaline earth metal;
the latter is reacted with a halogenated compound formula III:

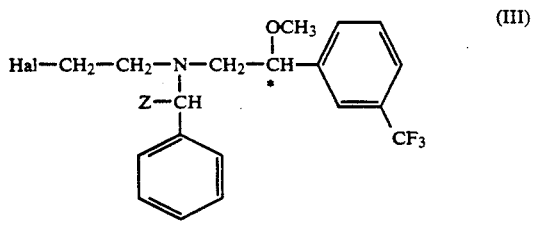

wherein:
Z represents a hydrogen atom or a methyl radical, and
Hal represents a halogen atom, such as a chlorine, bromine or iodine atom;

and the compound so obtained of formula IV:

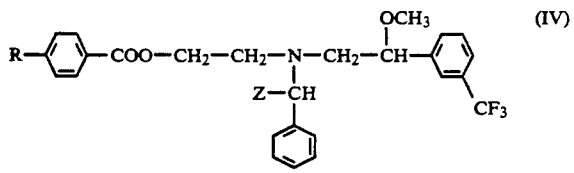

wherein R and Z have the meanings given hereinbefore, is catalytically debenzylated.

The compounds of formula III wherein Z represents a hydrogen atom result in racemic compounds IV.

The compounds of formula III wherein Z represents a methyl radical result either in racemic compounds IV or in laevorotatory or dextrorotatory enantiomers depending on whether the α-methylbenzyl group bonded to the nitrogen atom is RS, S or R, respectively.

Certain starting compounds of formula II:

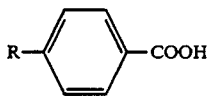

are known.

This is true of acids of formula II wherein R represents:
a hydrogen atom (in which case the compound II is benzoic acid, a commercial product)
or a group:

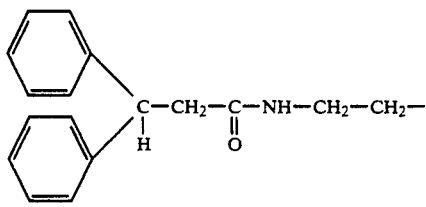

cf: European Journal of Pharmacology (1987), 141-2, 243-251;
or the fluoren-9-ylacetylaminoethyl radical, cf.: U.S. Pat. No. 4,136,197.

In the other cases, that is to say when R represents a:

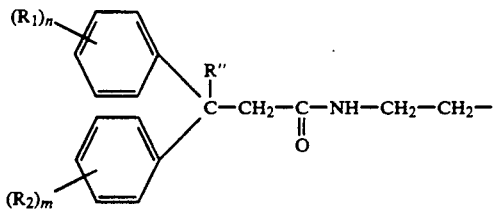

group wherein $R_1$, $R_2$, $R''$, n and m are as defined hereinbefore but, in addition, $R_1$, $R_2$ and $R''$ do not simultaneously represent a hydrogen atom, the corresponding compounds II are new products which, as such, form part of the present invention.

There are thus included within the present invention, as new starting materials that can be used for the synthesis of compounds of formula I - which can themselves be used as medicaments - compounds II corresponding more specifically to formula IIa:

wherein $R_a$ represents a group of formula A:

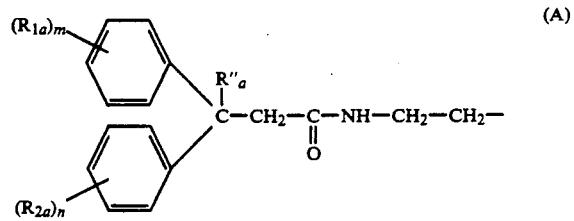

wherein:
m and n have the meanings given hereinbefore,
$R''_a$ represents a hydrogen atom or a straight-chain or branched alkyl radical containing from 1 to 5 carbon atoms, and
$R_{1a}$ and $R_{2a}$, which are the same or different, each represents a hydrogen atom or a straight-chain or branched alkyl or alkoxy radical each having from 1 to 5 carbon atoms, with the proviso, however, that $R_{1a}$, $R_{2a}$ and $R''_a$ do not simultaneously represent a hydrogen atom.

The compounds II that are novel were prepared by converting acids of formula V:

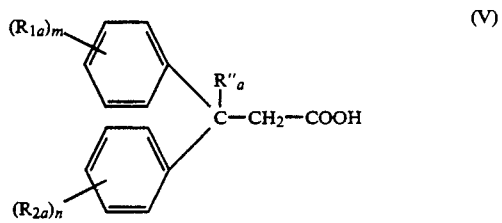

wherein $R''_a$, $R_{1a}$, $R_{2a}$, m and n have the meanings given hereinbefore, into an acid chloride or mixed anhydride of formula $V_a$ or $V_b$ respectively:

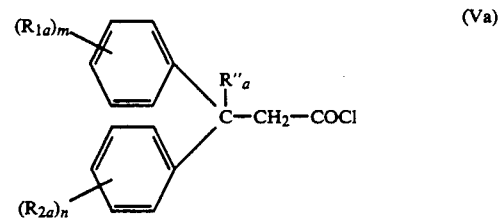

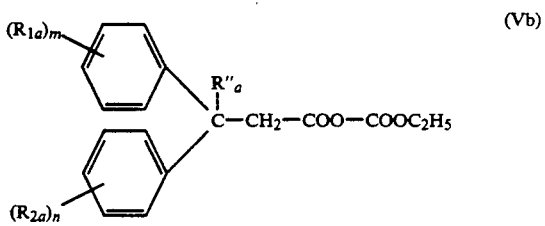

which are condensed a) either with an amino acid of formula VIa:

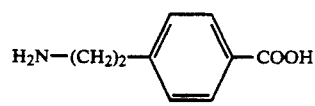 (VIa)

to obtain a compound of formula IIa directly, a formula which can be more precisely drawn as follows:

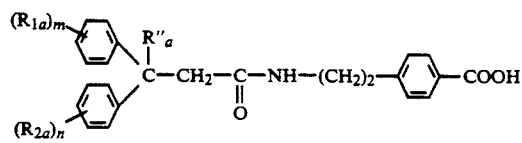 (IIa)

wherein $R''_a$, $R_{1a}$, $R_{2a}$, m and n have the meanings given hereinbefore, b) or with an amino ester of formula VIb:

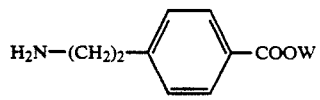 (VIb)

wherein W is a straight-chain or branched alkyl radical having from 1 to 5 carbon atoms, to yield a compound of the general formula II'a:

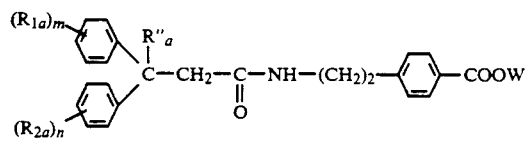 (II'a)

wherein $R''_a$, $R_{1a}$, $R_{2a}$, m, n and W have the meanings given hereinbefore,
which is hydrolysed to form an acid of formula IIa.

In the case where $R''_a$ represents a hydrogen atom, the corresponding acids V were themselves obtained by HORNER reaction between the ketone of formula B:

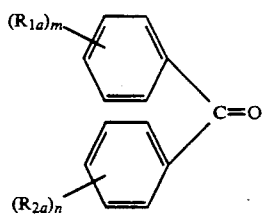 (B)

and ethyl phosphonoacetate [(C₂H₅O)₂OP—CH₂—COOC₂H₅], followed by catalytic hydrogenation of the resulting compound of formula C:

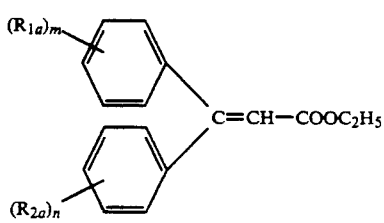 (C)

to yield the ester of formula D:

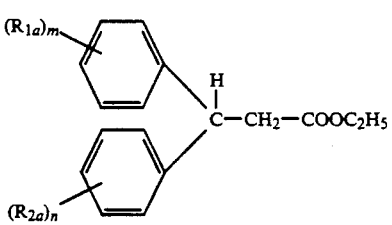 (D)

which is then hydrolysed to form the corresponding acid of formula E:

(E)

($R_{1a}$, $R_{2a}$ m and n in each of the formulae having the meanings given hereinbefore), that is to say to form the acid V wherein R″ represents a hydrogen atom.

In the case where $R''_a$ represents a straight-chain or branched alkyl radical containing from 1 to 5 carbon atoms, the corresponding acids V were themselves obtained by COPE condensation between the ketone of formula B':

(B')

(wherein $R_{1a}$ and m are as defined hereinbefore and Alk represents a straight-chain or branched alkyl radical containing from 1 to 5 carbon atoms)
and ethyl cyanoacetate (NC—CH₂—COOC₂H₅) in toluene, in the presence of acetic acid and ammonium acetate, to yield the ethylene compound of formula F:

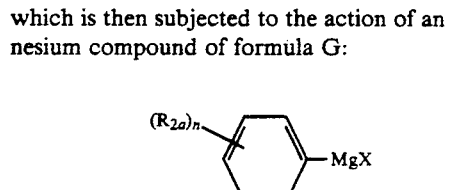 (F)

which is then subjected to the action of an organomagnesium compound of formula G:

 (G)

($R_{2a}$ and n being as defined hereinbefore and X representing a halogen atom)
to yield the compound of formula H:

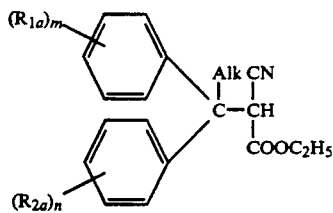
(H)

(wherein $R_{1a}$, $R_{2a}$, m, n and Alk are as defined hereinbefore), which compound H is hydrolysed to form the acid of formula J:

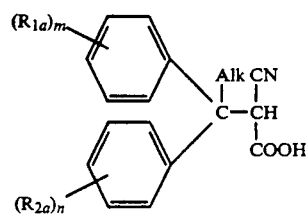
(J)

which is decarboxylated to yield the nitrile of formula K:

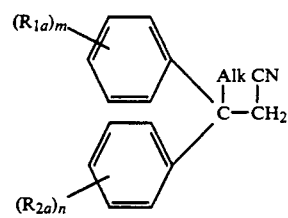
(K)

which is in turn hydrolysed to form the desired acid of formula L:

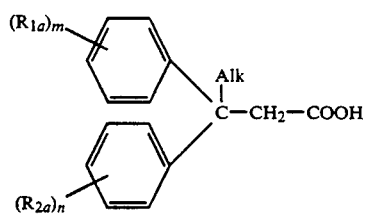
(L)

(wherein $R_{1a}$, $R_{2a}$, m, n and Alk are as defined hereinbefore); that is to say to form an acid of formula V wherein $R''_a$ represents a straight-chain or branched alkyl radical containing from 1 to 5 carbon atoms.
The starting materials of the general formula III:

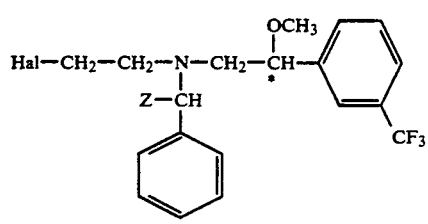
(III)

wherein Hal and Z are as defined hereinbefore, were obtained in accordance with the following reaction procedure:

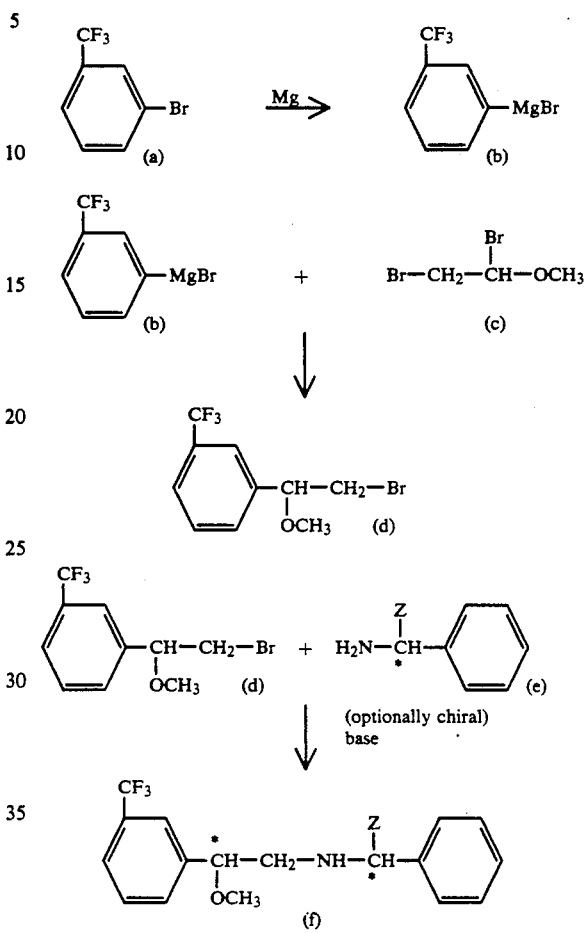

and the latter is recrystallised in hydrochloride form. When Z represents a methyl radical, depending on whether the starting α-methylbenzylamine is R or S, the hydrochloride of compound (f) is obtained by recrystallisation in the form of one or the other diastereoisomer.

The benzylated amine of formula f (optionally in pure diastereoisomer form) is then alkylated by means of ethyl bromoacetate in the presence of a base, such as potassium carbonate, to yield the compound of formula g:

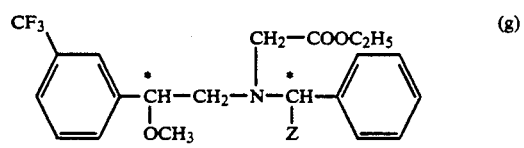
(g)

which is then reduced with $LiAlH_4$ to form the alcohol of formula h:

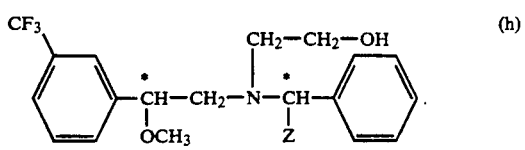
(h)

The latter is then converted into the halide III by means of a halogenated compound (such as, for example, SOCl₂, PCl₅ or POCl₃ to obtain, more precisely, a compound of formula III wherein Hal represents a chlorine atom, that is:

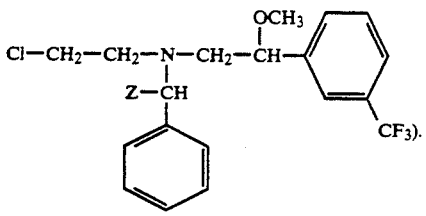

The present invention also relates to a process for the preparation of compounds of the general formula I which is characterised in that:
a primary acid (optionally chiral) of formula VII:

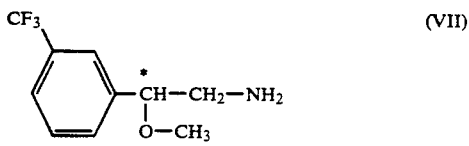

is reacted with ethylene oxide to obtain the compound of formula VIII:

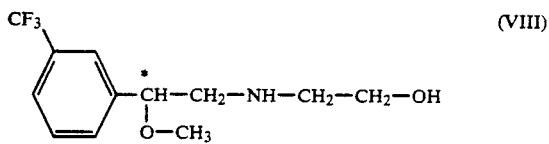

which is converted into the chloride of formula IX:

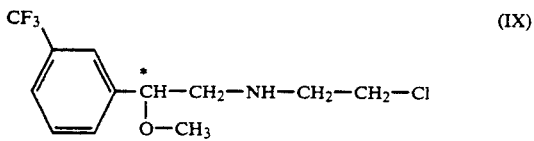

and the latter is coupled with a salt of formula II':

wherein R and M are as defined hereinbefore, to yield a compound of formula I:

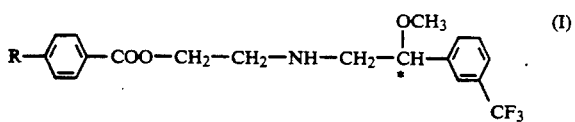

The compounds of formula I can be converted into addition salts with acids, which salts, as such, form part of the present invention.

There may be mentioned as acids for the formation of those salts, for example, in the mineral series, hydrochloric, hydrobromic, nitric, sulphuric and phosphoric acid and, in the organic series, acetic, propionic, maleic, fumaric, tartaric, oxalic, benzoic, methanesulphonic and isethionic acid.

The compounds of formula I and their physiologically tolerable addition salts have valuable pharmacological and therapeutic properties, especially properties regulating the metabolism of glucides and lipids. Moreover, they cause a moderate reduction in arterial pressure.

More precisely, the compounds of the present invention improve the efficacy of insulin at a peripheral and/or hepatic level, resulting in an improvement in glucose tolerance and in moderate hyperglycemia, where it exists, without the risk of hypoglycemia, as well as in a reduction in hyperinsulinemia. Furthermore, the compounds of the present invention reverse insulin resistance induced by high levels of amylin.

They also reduce hypertriglyceridemia and combat LDL (low density lipoprotein) oxidation, which has an implication in the prevention of macroangiopathies.

They cause a modest reduction in weight associated with a reduction in food intake, not associated with a serotoninergic mechanism, and as a result of the latter two properties they are differentiated from existing products in that field (benfluorex, fenfluramine).

Those properties enable them to be used therapeutically especially for the treatment of non-insulin-dependent diabetics not treated by diet, non-insulin-dependent diabetics treated with blood sugar-reducing medicaments, diabetics that are insulin-dependent or not treated with insulin, or non-hyperglycemic, hypertensive or non-hypertensive, patients having hyperinsulinemia (i.e. android obesity) and all exhibiting a resistance to insulin, induced or not by amylin.

The products of the invention are thus used in the treatment of diabetes, obesity, syndrome X (by way of improvement in the effect of insulin at the periphery and/or with respect to the liver, decrease in triglycerides and in LDL oxidation, associated with a moderate reduction in weight), and in the treatment of hypertension in patients who are resistant to insulin or have associated or unassociated metabolic anomalies such as, for example, hyperinsulinemia, dyslipemia and hyperglycemia, these having been induced or not by amylin.

The present invention also relates to pharmaceutical compositions comprising as active ingredient a compound of formula I or a physiologically tolerable salt thereof, mixed with or in association with one or more appropriate pharmaceutical excipients.

The so-obtained pharmaceutical compositions are generally presented in dosage form comprising from 25 to 100 mg of active ingredient. They may be in the form of tablets, dragees, capsules, suppositories or injectable or drinkable solutions, and may be administered by the oral, rectal or parenteral route.

The dosage may vary, especially in accordance with the age and weight of the patient, the route of administration, the nature of the disorder and associated treatments, and ranges from 25 to 100 mg of active ingredient per administration from 1 to 4 times per day.

The following Examples illustrate the invention.

EXAMPLE 1

Levorotatory isomer of 2-[(β-methoxy-β-meta-trifluoromethylphenyl)ethylamino]ethyl para-[2-(α-fluoren-9-ylacetylamino)ethyl]benzoate hydrochloride

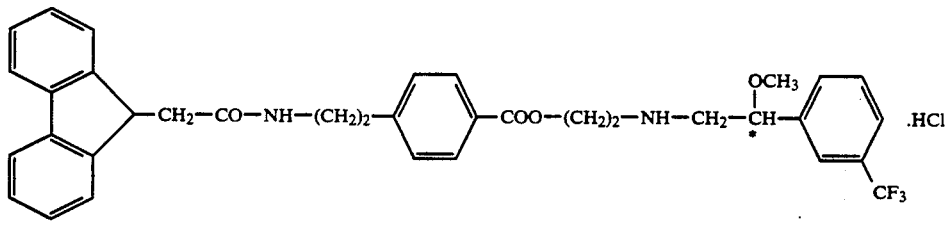

8.3 g of 1-N-(β-chloroethyl)-N-(α-phenylethyl)-N-[(β-methoxy-β-meta-trifluoromethylphenyl)ethyl]amine hydrochloride are stirred in 100 ml of water, 100 ml of ether and 2.5 ml of concentrated sodium hydroxide solution. The ethereal phase is collected by decanting, and dried over MgSO₄; the solvent is distilled off and the residue is dissolved in 50 ml of anhydrous dimethylformamide.

That solution is then slowly poured into a flask containing 7.3 g of para-[2-(fluoren-9-ylacetylamino)ethyl]benzoic acid, 2.7 g of K₂CO₃ and 100 ml of dimethylformamide, which together have beforehand been heated at 60° C. for 45 minutes.

After the addition of the chlorinated compound, the reaction mixture is heated to 90° C. for 3 hours under nitrogen. The solvent is distilled off in vacuo and the residue is taken up in ether. The potassium chloride precipitate is filtered off and the ether is distilled off. The residue obtained (approximately 13 g) is filtered through 300 g of silica using a mixture of dichloromethane/ethyl acetate (95/5) as eluant.

In this manner 8 g of compound IV of formula:

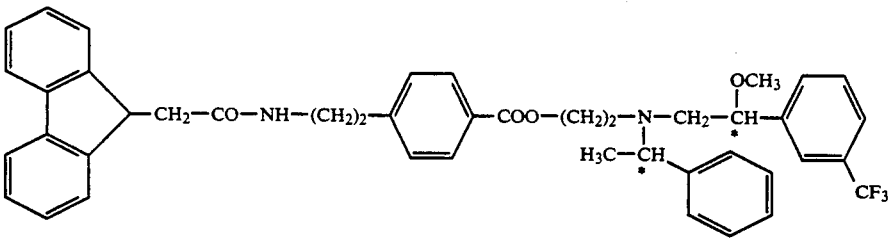

are obtained. 7 g of that compound dissolved in 160 ml of anhydrous isopropanol are hydrogenated under a hydrogen pressure of approximately 90 lbs, at a temperature of 50° C., until complete absorption of the necessary amount of hydrogen.

The solution is then filtered through talc, the solvent is distilled off and the residue is filtered through 100 mg of silica using a CH₂Cl₂/CH₃COOC₂H₅ mixture (50/50) as eluant.

The solvent is distilled off from the fraction containing the product. The residual oil is taken up in ether and a slight excess of ethereal hydrogen chloride solution is added. The resulting precipitate is filtered and washed with ether, yielding 4.5 g of the levorotatory isomer of 2-[(β-methoxy-β-meta-trifluoromethylphenyl)ethylamino]ethyl para-[2-(α-fluoren-9-ylacetylamino)ethyl]benzoate hydrochloride.

Rotatory power: (c=1% in ethanol).
[α]589: −29.7
[α]578: −30.6
[α]546: −34.7
[α]436: −58.3
[α]365: −90.9.

The para-[2-(fluoren-9-ylacetylamino)ethyl]benzoic acid starting material was prepared in accordance with U.S. Pat. No. 4,136 197.

The 1-N-(β-chloroethyl)-N-(α-phenylethyl)-N-[(β-methoxy-β-meta-trifluoromethylphenyl)ethyl]amine hydrochloride starting material was prepared as follows:

a) 225 g of 3-trifluoromethylbromobenzene are added dropwise to a mixture of 27 g of magnesium and 500 ml of anhydrous ether to which an iodine crystal has previously been added. The reaction is affected in such a manner as to ensure a slight reflux of the ether. Once the magnesium has dissolved, 232 g of 1-methoxy-1,2-dibromoethane (prepared in accordance with the technique described in Organic Syntheses vol. IV, p 748, replacing the ethanol with methanol) are slowly added.

Refluxing is maintained for 1 hour once addition is complete. The mixture is then cooled and subsequently hydrolysed with 250 ml of water. After decanting, the ethereal phase is washed with water and then dried.

The solvent, and then the product, are distilled off under reduced pressure. 203 g of 3-trifluoromethyl-1-(2-bromo-1-methoxyethyl)benzene are obtained (b.p.₁₃ Pa=68° C.).

b) 202 g of that brominated compound and 173 g of (S)-α-methylbenzylamine are refluxed in 714 ml of xylene for 6 hours.

The xylene is then distilled off and the residue is taken up in ether. The α-methylbenzylammonium bromide is removed from the resulting filtrate, which is then distilled to yield 144 g of product which boils at 125°-128° C. under 13 Pa.

94 ml of 5N ethereal hydrogen chloride are added to that compound dissolved in ether. The resulting precipitate is filtered, washed with ether and recrystallised twice from 550 ml of isopropanol each time, yielding 80 g of the pure diastereoisomer.

c) 21 g of the latter are reacted with 12 g of ethyl bromoacetate and 9.8 g of potassium carbonate in 65 ml of anhydrous ethanol. The reaction mixture is refluxed for 8 hours, 2 ml of ethyl bromoacetate and 2.5 g of potassium carbonate are then added, and the mixture is heated again for 4 hours. The mineral compound is filtered off, the ethanol and the excess bromoacetate are distilled off, and the oil which remains is used as such.

d) 27 g of the ester so obtained are reacted with 3.78 g of LiAlH$_4$ in 150 ml of anhydrous tetrahydrofuran under reflux for 5 hours.

The mixture is then hydrolysed with 3.8 ml of water, then with 3.8 ml of 4N NaOH and finally with 11.4 ml of water.

The organic phase is filtered and concentrated and used as such.

e) 22.9 g of the alcohol so obtained are dissolved in 65 ml of chloroform. 10.5 ml of 6N ethereal hydrogen chloride are added dropwise to the solution. The solvent is evaporated off, the residue is taken up in 65 ml of chloroform, and 8.2 g of thionyl chloride are added dropwise thereto.

The whole is refluxed for 5 hours and then the solvent is distilled off. The residue is taken up in 150 ml of ethyl acetate and dissolved with the application of heat. The mixture is allowed to cool until a slight precipitate is formed corresponding to:

[Structure: 3-CF$_3$-C$_6$H$_4$-CH(OCH$_3$)-CH$_2$-NH-*CH(CH$_3$)-C$_6$H$_5$ · HCl]

which is removed accordingly.

The solvent is then distilled off from the remaining solution and the product remaining (which is the 1-N-(β-chloroethyl)-N(α-phenylethyl)-N-[(β-methoxy-β-meta-trifluoromethylphenyl)ethyl]amine hydrochloride) is used as such.

EXAMPLES 2 TO 7

The following compounds were prepared by proceeding as described in Example 1:

2. Dextrorotatory isomer of 2-[(β-methoxy-β-meta-trifluoromethylphenyl)ethylamino]ethyl para-[2-(α-fluoren-9-ylacetylamino)ethyl]benzoate hydrochloride, rotatory power (c=1% in ethanol):
[α]589: +30.0
[α]578: +31.3
[α]546: +35.8
[α]436: +61.4
[α]365: +95.0.

3. dl-2-[(β-methoxy-β-meta-trifluoromethylphenyl)ethylamino]ethyl para-[2-(α-fluoren-9-ylacetylamino)ethyl]benzoate hydrochloride.

4. Levorotatory isomer of 2-[(β-methoxy-β-meta-trifluoromethylphenyl)ethylamino]ethyl para-[2-(benzhydrylacetylamino)ethyl]benzoate hydrochloride. Rotatory power (c=1% in ethanol at 21° C.):
[α]589: −32.3
[α]578: −33.5
[α]546: −38.1
[α]436: −64.5
[α]365: −100.7

5. dl-2-[(β-methoxy-β-meta-trifluoromethylphenyl)ethylamino]ethyl benzoate hydrochloride, m.p. (Kofler): 122°–123° C.

6. Levorotatory isomer of 2-[(β-methoxy-β-meta-trifluoromethylphenyl)ethylamino]ethyl benzoate hydrochloride.

Rotatory power (c=1% in ethanol at 23° C.):
[α]589: −52.9
[α]578: −55.1
[α]546: −62.7
[α]436: −106.6
[α]365: −167.3.

7. Dextrorotatory isomer of 2-[(β-methoxy-β-meta-trifluoromethylphenyl)ethylamino]ethyl benzoate hydrochloride.

Rotatory power (c=1% in ethanol at 23° C.):
[α]589: +51.5
[α]578: +53.9
[α]546: +61.1
[α]436: +103.6
[α]365: +152.2

EXAMPLES 8 and 9

The new starting materials of the formula IIa were prepared in accordance with the method illustrated in the following Examples:

8. Para-{2-[N-(bis-4,4'-n-pentyloxybenzhydrylacetyl)amino]ethyl}benzoic acid

[Structure: bis(4-CH$_3$-(CH$_2$)$_4$-O-C$_6$H$_4$)CH-CH$_2$-CO-NH-(CH$_2$)$_2$-C$_6$H$_4$-COOH]

a) Para-n-pentyloxybromobenzene: 276 g of anhydrous potassium carbonate are added to 173 g of p-bromophenol dissolved in 1800 ml of methanol. After stirring, the reaction mixture is treated with 164 ml of n-bromopentane and maintained at reflux for 4 hours with stirring.

After cooling, 3 liters of water are added and the methanol is removed under water-jet vacuum.

After extraction with 2 liters of ether and then twice with 1 liter of ether each time, the organic solutions are combined and washed 3 times with 1 liter of water each time. After drying over anhydrous MgSO$_4$, the solvent is evaporated off in vacuo and the residue is distilled.

222.8 g of para-n-pentyloxybromobenzene (b.p./$_{13}$ $P_a$=87°–91° C.) are obtained. Yield: 91.6%. b) Para-n-pentyloxybenzaldehyde: by operating as above starting with 33 g of para-hydroxybenzaldehyde, 74.5 g of potassium carbonate and 45 g of n-bromopentane, 21 g of para-n-pentyloxybenzaldehyde (b.p./$_{1.3}$ $P_a$=112°–114° C.) were isolated. Yield: 37%.

c) Ethyl n-pentyloxybenzylidenemalonate: 32.6 g of dimethylamine hydrochloride and 1.7 g of potassium fluoride are added to 38.5 g of para-n-pentyloxybenzaldehyde and 31 ml of ethyl malonate dissolved in 400 ml of anhydrous dimethylformamide. The reaction mixture is heated with stirring for 18 hours. After the mixture has been cooled, the solvent is evaporated off in vacuo ($13 \times 10^2$ to $20 \times 10^2$ Pa). The residue is taken up twice in 250 ml of methylene chloride. The organic layer is washed with 200 ml of a normal hydrochloric acid solution and then twice with 200 ml of water.

After drying over anhydrous magnesium sulphate, the solvent is evaporated off under water-jet vacuum. Distillation of the residue yields 49.8 g of ethyl para-n-pentyloxybenzylidenemalonate (b.p./$_{13\ Pa}$=170°–175° C.). Yield: 74.5%.

d) Ethyl α-ethoxycarbonyl-β,β-[bis(para-n-pentyloxyphenyl)]propanoate:

To a solution of para-n-pentyloxyphenylmagnesium bromide prepared from 5.8 g of para-n-pentyloxybromobenzene and 0.64 g of magnesium turnings in 30 ml of tetrahydrofuran (THF) (poured in over a period of 1 hour under reflux, then maintained at reflux for a further 1 hour) there are added, over a period of 30 minutes, 8 g of ethyl para-n-pentyloxybenzylidenemalonate dissolved in 25 ml of THF. After refluxing for 2 hours 30 minutes with stirring, 25 ml of a normal HCl solution are poured in. The reaction mixture is extracted three times with 50 ml of water each time and then dried over MgSO$_4$. After evaporation the residue is purified by chromatography. 8.7 g of the desired product are obtained.

e) β,β-[Bis(para-n-pentyloxyphenyl)]propionic acid:
8.5 g of the product obtained in d) dissolved in 22.5 ml of ethanol are added to a solution of 6.2 g of potassium hydroxide in 100 ml of water. The solution obtained is maintained at reflux for 1 hour 30 minutes. After removal of the solvent under water-jet vacuum, the residue is taken up in 200 ml of water and then acidified with 11 ml of a 37% concentrated HCl solution. The resulting oil is extracted 3 times with 100 ml of ether each time. After washing twice with 50 ml of water each time, the ether is dried over magnesium sulphate and then evaporated in vacuo. 5.6 g of product, m.p.: 134°–136° C., are obtained, yield: 75%.

The residue is heated for 15 minutes at 180°–190° C. After washing with petroleum ether, 3.3 g of β,β-[bis-(para-pentyloxyphenyl)]propionic acid is obtained, m.p.: 72° C., yield: 67%.

f) Ethyl para-{2-[N-(bis-4,4'-n-pentyloxybenzhydrylacetyl)amino]ethyl}benzoate:

1.07 ml of triethylamine in 10 ml of THF are added to 3.06 g of the acid prepared in e) dissolved in 30 ml of THF. After stirring for 1 hour, the resulting solution is added to 0.76 ml of ethyl chloroformate in 30 ml of THF cooled to 0° C. 1.56 g of ethyl para-[β-(amino)ethyl]benzoate dissolved in 10 ml of THF are then poured in over a period of 15 minutes. The temperature rises to 10° C. After 45 minutes' stirring at room temperature and 12 hours under reflux, the precipitate is suction-filtered off and the filtrate is evaporated to dryness in vacuo. Chromatography yields 3.06 g of the desired benzoate.

g) Para-{2-[N-(bis-4,4'-n-pentyloxybenzhydrylacetyl)amino]ethyl}benzoic acid:

3 g of the ester obtained in f), 15 ml of ethanol and 5.7 ml of normal sodium hydroxide solution maintained at reflux for 2 hours result in the corresponding benzoic acid.

9. Para-{2-[N-(3-methyl-3,3-diphenylpropionyl)amino]ethyl}benzoic acid:

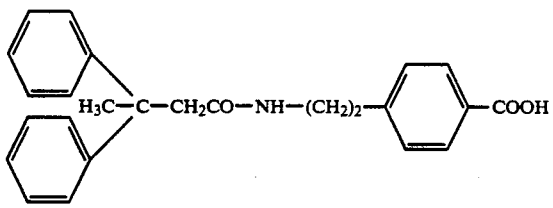

a) Ethyl (α-methylbenzylidene)-cyanoacetate:

60 g of acetophenone, 56.6 g of ethyl cyanoacetate, 7.7 g of ammonium acetate, 24 g of acetic acid and 100 ml of benzene are refluxed with stirring and the water formed during the course of the reaction is removed as the reaction proceeds using a Dean Stark apparatus.

After 13 hours 40 minutes of heating, 100 ml of ether are added and the reaction mixture is washed 3 times with 100 ml of water each time. The organic layer is dried over magnesium sulphate and concentrated under water-jet vacuum and the residue is distilled, yielding 58.4 g of ethyl (α-methylbenzylidene)-cyanoacetate (b.p./$_{13\ Pa}$=125°–128° C.).

b) α-Ethoxycarbonyl-β,β-diphenylbutyronitrile:

41 g of bromobenzene dissolved in 100 ml of anhydrous ether are added over a period of 1 hour 20 minutes, with stirring, to 6.3 g of magnesium turnings and 240 ml of anhydrous ether. The mixture is refluxed for 2 hours and then, over a period of 30 minutes, 51 g of ethyl(α-methylbenzylidene)-cyanoacetate in 150 ml of ether are added. After having been heated for 5 hours, the reaction mixture is hydrolysed with 150 ml of 2N HCl. The organic layer is decanted. The aqueous layer is extracted twice with 100 ml of ether each time. The ethereal phases are combined, washed with 100 ml of water, dried over MgSO$_4$ and, after filtration, concentrated under water-jet vacuum.

Distillation of the residue yields 30.7 g of the desired product (b.p./$_{13\ Pa}$=150°–155° C.), yield: 46%.

c) α-Carboxy-β,β-diphenylbutyronitrile:

15 g of α-ethoxycarbonyl-β,β-diphenylbutyronitrile, 65 ml of ethanol, 18.4 g of potassium hydroxide pellets and 30 ml of water are stirred at room temperature for 4 hours. After concentration in vacuo, the residue is taken up in 150 ml of water. After extracting 3 times with 50 ml of ether each time, the aqueous layer is acidified with 22 ml of concentrated HCl and extracted 3 times with 100 ml of ether each time. The organic layers are combined, dried over MgSO$_4$ and evaporated. 14 g of the desired product are obtained.

d) β,β-Diphenylbutyronitrile:

14 g of α-carboxy-β,β-diphenylbutyronitrile and 85 ml of triethylene glycol are heated at 80° C. for 30 minutes and then, after cooling, diluted with 300 ml of water. After extracting 3 times with 150 ml of ether each time, drying the organic layer and concentrating in vacuo, and purifying by chromatography, 7.3 g of β,β-diphenylbutyronitrile are obtained. Yield: 64%.

e) β,β-Diphenylbutyric acid:

7.2 g of the product obtained in d), 9.6 ml of concentrated sulphuric acid, 12 ml of water and 12 ml of acetic acid are maintained at reflux for 22 hours. After cooling and treating with 90 ml of water, the resulting precipitate is suction-filtered and washed with water. After drying and recrystallisation from 20 ml of cyclohexane, 6.5 g of the desired acid are obtained, m.p. 100° C., yield: 77%.

f) $\beta,\beta$-Diphenylbutyryl chloride:

6.5 g of the acid above are added over a period of 15 minutes to 10 ml of thionyl chloride. After heating for 2 hours at reflux, the solution obtained is concentrated in vacuo and the residue is taken up twice with 50 ml of benzene with evaporation each time. 6.6 g of $\beta,\beta$-diphenylbutyryl chloride are obtained.

g) Para-{2-[N-(3-methyl-3,3-diphenylpropionyl)amino]ethyl}benzoic acid:

31.5 g of triethylamine are added, with stirring, to a suspension of 5.2 g of para-[$\beta$-(amino)ethyl]benzoic acid hydrochloride in 200 ml of anhydrous dimethylformamide, then 6.5 g of the chloride obtained in f) dissolved in 75 ml of anhydrous THF are poured in over a period of 15 minutes. The temperature rises from 26° to 34° C. After stirring for 4 hours at room temperature, then for 5 hours at 40° C., the triethylamine hydrochloride formed is suction-filtered off and the filtrate is concentrated in vacuo. The residue is taken up in 60 ml of water. The precipitate formed is suction-filtered, dried in air and then recrystallised from 50 ml of anhydrous isopropanol. 5 g of para-{2-[N-(3-methyl-3,3-diphenylpropionyl)amino]ethyl}benzoic acid are obtained, m.p.: 211° C.

EXAMPLE 10

Pharmacological Study

A. Study of the Effect of an Acute Treatment Administered by Portal Perfusion to Conscious Rats 1. Aim of the experiment The technique of portal perfusion in conscious rats makes it possible to study the effect of pharmacological substances on modifications of the tolerance to glucose administered by the intravenous route.

The injections of agents directly into the portal circulation makes it possible to avoid the effects of gastric transit, absorption and release of hormone through the intestinal wall and thus to explore:
both the direct effect on the hepatic tissue
and the existence of a liver-central nervous system-peripheral tissue relay (liver, muscle or endocrinal target).

2. Protocol 2.1 Animals used

In this experiment, adult male SPRAGUE DAWLEY rats were used in groups of 5 to 12 animals.

The rats used, aged 52 weeks, exhibit
a reduction in glucose tolerance,
an increase in basal insulinemia, and
an increase in plasma lipids.

The housing (from 9 to 52 weeks) of these rats was effected in a chamber at a temperature regulated at from 21° to 22° C. subjected to a fixed cycle of light (from 7.30 to 19.30 hours) and darkness (from 19.30 to 7.30 hours). Their food consisted of a maintenance diet (UAR A 03); water and food were supplied "ad libitum", with the exception of the night-fasting preceding the tests, when the food was removed.

2.2 Methods

Surgical preparation:

On $d_7$ before the beginning of the experiment, the rats are anaesthetized with ketamine (IMALGENE 1000-Rhone MERIEUX), and a Silastic catheter (602-135, medical grade, DOW CORNING MIDLAND) is implanted in the hepatic portal vein [cf. Strubbe J. H., Wolsink J. G., Schutte A. M., Balkan B., and Prins A. J. A.: Hepatic-portal and cardiac infusion of CKK-8 and glucagon induce different effects on feeding. Physiology and Behavior 46, 643–646 (1989)] for the perfusion of physiological solute (day control) and then the product to be tested. They are then placed individually in plexiglass cages.

After recovery, that is to say approximately 10 days later, a second Silastic catheter (602-155, medical grade, DOW CORNING MIDLAND) is introduced up into the right auricle through the right jugular vein [cf. Steffens A. B.: Method for frequent sampling of blood and continuous infusion of fluids in the rat without disturbing the animal. Physiology and behavior 4, 833–836 (1969)]. During the test, various blood samples will be taken and the intra-cardiac injection of a glucose bolus will be carried out using that catheter.

During the two surgical procedures, the catheters are slid under the skin and exited at the top of the head by means of a polished needle bent back and plugged by a polyethylene (PE) cap closed with the candle.

0.4 ml of a 500 U/ml heparin solution (ROUSSEL UCLAF) followed by 0.1 ml of PVP (30% polyvinylpyrrolidone solution-MW 25000-MERCK) are introduced into the catheters before closure with the polyethylene cap.

The viscosity of the PVP makes it possible to avoid a reflux of blood into the catheter.

The day before each experiment, the rats are subject to 18 hours of night fasting. On the day of the experiment these rats are weighed and the catheters are checked to ensure they are working properly.

In order to eliminate the stress of connecting the catheters to the externalised needles on top of the head, 20 minutes' rest is required before the experiment is started.

The intraportal perfusions, carried out using a No. 3 polyethylene catheter, take 60 minutes; they have a constant flow of 2 ml/hour, that is to say approximately 0.033 ml/minute, ensured by a BRAUN perfuser. An IVGTT test (intravenous administration glucose tolerance test) is carried out 30 minutes after the beginning of the portal perfusion.

The control experiment (reference test) consists in the perfusion of a saline solution (0.9% isotonic sodium chloride BIOSEDRA), which permits the determination of the basal value of tolerance (K) towards a dose of glucose for each rat.

In normal rats, insulin resistance can be induced by an intraportal infusion of amylin (IAPP, insulinoma associated pancreatic polypeptide) at 26 nmoles/kg/h for 90 minutes.

0.40 ml blood samples are taken (No. 6 polyethylene catheter) immediately before the perfusion and 30 minutes after the beginning of the perfusion. These samples are used to determine the basal glycemia and basal insulinemia. Immediately after collecting basal no. 2, that is to say 30 minutes after the beginning of the perfusion, a glucose bolus is administered (1 ml/kg of a 50% glucose solution) into the jugular vein. A series of samples are then taken every 3 minutes from t+30 to t+60 minutes after administration of the bolus. A 0.40 ml volume is taken each time and replaced by 0.40 ml of physiological heparin serum.

Satisfactory functioning of the catheters is ensured by injecting PVP between each experiment.

Collection of the samples:

To determine the glycemia, the blood is collected in URAC (deproteinating solution) using 20 µl of blood per 200 µl of URAC (1/10 dilution).

The samples destined for the determining the insulinemia are collected over heparin (20 µl of physiological heparin serum at 500 Ul/ml, that is 7.5 Ul of heparin per tube to be centrifuged).

All the tubes are placed in ice as soon as the samples are collected. The samples are then centrifuged for 10 minutes at 3000 revs/min (refrigerated centrifuge) to separate the substances present as quickly as possible.

The sera (in URAC for glycemia) and the plasmae (insulinemia) are then distributed into Eppendorf tubes which are placed in the freezer (−20° C.) until the day of the determination.

Analytical procedures:
Determination of the glycemia:

Determination of the insulinemia:

Immunoreactive plasma insulin (IRI) is determined by a PHARMACIA Phadeseph kit radioimmunological method, a solid-phase double antibody technique.

The determination of the standards and of the samples is carried out in duplicate.

Preparation of the solutions:
For the control experiment (reference test):
Intraportal perfusion of 0.9% isotonic sodium chloride (BIOSEDRA)

For the intraportal perfusion of the pharmacological reactant:

A stock solution with 1 mg of base product per ml of distilled water is produced and used to prepare the final solution (in 0.9% NaCl).

Results

The results are given in the following Tables Ia and Ib.

TABLE Ia

| SDCD male rats 52 weeks | Basal insulinemia µU/ml % change | Peak insulinemia µU/ml % change | Insulinemia 30 min after glucose µU/ml % change | Glucose tolerance $K10^{-2}$ % |
|---|---|---|---|---|
| Control | $24.06 \pm 3.03$ | $57.4 \pm 13.7$ | $29.0 \pm 3.7$ | $2.72 \pm 0.23$ |
| Benfluorex 7.5 µg/kg/min × 60 min | −42% $p < 0.05$ | −5% NS | −36% NS | +50% $p = 0.025$ |
| Dimethyl biguanide 15 µg/kg/min × 60 min | | inactive | | |
| Product of Example 1 | | | | |
| 0.25 µg/kg/min × 60 min | −42% $p < 0.05$ | 0 | −21% NS | +3% NS |
| 0.50 µg/kg/min × 60 min | −6% $p < 0.01$ | −21% NS | −69% $p < 0.001$ | +40% $p = 0.025$ |
| 0.75 µg/kg/min × 60 min | −25% $p = 0.05$ | +10% NS | −36% NS | +60% $p = 0.005$ |

An intraportal catheter and an intracardiac catheter (right auricle) are implanted in 52-week-old SDCD rats. After post-surgical recovery, the various groups of rats are subjected to an 18-hour fast. The rats are conscious during the experiment. The products are administered by intraportal perfusion for a period of 1 hour. An induced hyperglycaemia test is effected 30 minutes after the beginning of the perfusion which is continued during the IVGTT.

TABLE Ib

Insulin resistance induced by an intraportal infusion of amylin to 12-week-old SD rats

| | Basal insulin levels (µU/ml) | Peak insulin levels (µU/ml) | Insulin levels 24 min after glucose (µU/ml) | Glucose tolerance $K \cdot 10^{-2}$ |
|---|---|---|---|---|
| Control | $5.93 \pm 0.48$ | $24.80 \pm 1.86$ | $8.86 \pm 0.77$ | $3.54 \pm 0.24$ |
| Amylin | $6.87 \pm 0.77$ | $23.54 \pm 1.7$ | $15.28 \pm 1.90$ | $1.71 \pm 0.27$ |
| Amylin + product of Example 1 (0.75 µg/kg/min for 60 mn) | $8.26 \pm 1.15$ | $23.60 \pm 2.17$ | $15 \pm 1.86$ | $3.79 \pm 0.38$ |

The blood glucose is measured by the glucose oxidase method using a Boehringer kit.

A quality control is effected by determining standard values and control values.

Measurement of glucide assimilation:

(cf. Conard v.: Mesure de l'assimilation du glucose, bases théoriques et applications cliniques [Measurement of the assimilation of glucose, theoretical basis and clinical applications], "acta medica belgica" editions (1959)).

The rate of glucose desappearance following glucose loading is expressed by the angular coefficient K of the straight line log c=log A−Kt obtained on semilogarithmic paper entering the time (min) on the abscissa and the ln [glucose] on the ordinate. This coefficient is calculated for the glycemia values corresponding to the times between the 6th and the 30th minute after administration of the bolus. The calculation is carried out by a computer, using a linear regression program, after verification by graphic representation.

This coefficient of glucide assimilation is considered as a constant, characteristic of a given subject.

B. STUDY OF THE EFFECT OF A CHRONIC TREATMENT ADMINISTERED PER OS TO 52-WEEK-OLD MALE SDCD RATS

1. Aim of the experiment

The tests are carried out on rats that have weight anomalies associated with hyperinsulism and hyperglyceridemia.

The following are investigated:

on the one hand the effect of a prolonged treatment with the product of Example 1 and the reference substances on those anomalies, and on the other hand the consumption of glucose by the adipose tissue is measured in the basal state and in the presence of insulin ($10^{-9}$M).

2. Protocol 2.1 Animals used

Rats identical to those in the acute treatment study are used (cf. paragraph A-2.1 hereinabove), that is male SDCD rats aged 52 weeks.

2.2 Methods 9 days before the beginning of the experiment ($d_{-9}$), the rats are divided into groups by stratified randomisation based on weight.

5 days before the beginning of the experiment ($d_{-5}$) the rats are conditioned by administering a gum solution.

The first day of the experiment ($d_1$), the products to be tested are administered to the rats at different doses twice per day. More precisely, the products are administered suspended in the gum between 9.00 and 10.00 hours and 16.00 and 17.00 hours for 14 days. The treated animals are weighed daily.

On day 15 the rats (fasted for 18 hours) are sacrificed by decapitation. The blood is immediately collected in a cupule. An amount (50 μl) is transferred into 500 μl of uranyl acetate for determining the glycemia. An amount of 3 ml is transferred into a tube containing a solution of heparin (30 μl per 1 ml of whole blood) and centrifuged to separate the plasma. Another amount of 300 μl is transferred to a tube containing 15 μl of a solution of EDTA/NaF for determining the lactates.

Epididymal adipose tissue is taken for metabolic study immediately after sacrifice.

For each animal, two fragments of right and left epididymal tissue are minced with scissors and distributed in 6 incubation flasks. Three of those flasks contain 500 μl of medium and the others 500 μl of medium to which porcine insulin ($10^{-9}$M) has been added; the production of $CO_2$ is thus measured in triplicate for each of the rats from each group.

2.3 Results

The results are given in the following Table II

C IN VITRO STUDY OF LDL OXIDATION

A comparative study between the product of Example 1 and the reference substances (benfluorex, dimethyl biguanide) with respect to in vitro LDL oxidation was carried out.

The results are given in the following Table III.

TABLE III

|  | In vitro LDL oxidation | | Incorporation of oleate in the esters of cholesterol |
|---|---|---|---|
|  | by copper | by monocytes |  |
| Benfluorex | Inactive at $10^{-4}$ M | Inactive at $10^{-4}$ M | $-30\%$ at $10^{-5}$ M |
| Dimethylbiguamide $10^{-4}$ M | Inactive at $10^{-4}$ M | Inactive at $10^{-4}$ M | Inactive at $10^{-5}$ M |
| Product of Example 1 | $IC_{50} = 10^{-5}$ M | $IC_{50} = 10^{-5}$ M | $-70\%$ at $10^{-5}$ M |

D EXAMINATION INTO A HYPOTENSIVE EFFECT IN CONSCIOUS DOGS

The arterial pressure was measured by external pressure band (sphygmomanometer) on the tail of the dog, before and after treatment with the product of Example 1 at a dose of 5 mg/kg p.o.

The results are given in the following Table IV.

TABLE IV

| Product tested | Animal (number:n) | Decrease in arterial pressure (AP) | |
|---|---|---|---|
|  |  | systolic AP | diastolic AP |
| Product of Example 1 (5 mg/kg p.o.) | dog (n = 4) | $-2.4 \times 10^3$ Pa to $-3.6 \times 10^3$ Pa | $-3 \times 10^3$ Pa to $-5 \times 10^3$ Pa |

E. CONCLUSION

The results of the studies described above show the pharmacological and therapeutic value of the levorotatory isomer of 2-[(β-methoxy-β-meta-trifluoromethylphenyl)ethylamino]ethyl para-[2-(α-fluoren-9-ylacetylamino)ethyl]benzoate hydrochloride (a particularly representative example of the compounds of the present invention) and the originality and superiority thereof compared with reference substances known to be specifically adapted to the treatments in question.

We claim:

TABLE II

| Treatment of 52-week-old male SDCD rats | % weight change | Basal insulin-aemia μU/ml % change | Glycermia g/l % change | Glucose tolerance K $10^{-2}$ % change | Triglyceride g/l % change | Cholesterol g/l % change | Cerebral serotonin |
|---|---|---|---|---|---|---|---|
| Control | $+0.4\%$ | $32 \pm 2.4$ | $1.06 \pm 0.05$ | $3.01 \pm 0.24$ | $3.64 \pm 0.57$ | $1.1 \pm 0.14$ |  |
| Benfluorex |  |  |  |  |  |  |  |
| 1 mg/kg × 2 | $-2\%$ (NS) | $-10\%$ NS | $-10\%$ NS | $+30\%$ $p < 0.05$ | $-43\%$ $p = 0.025$ | $-20\%$ NS | Reduced |
| 2.5 mg/kg × 2 | $-6\%$ $p = 0.85$ | $-16\%$ NS | $-12\%$ NS | $+25\%$ $p = 0.05$ | $-44\%$ $p = 0.05$ | $-30\%$ NS | Reduced |
| Product of Example 1 |  |  |  |  |  |  |  |
| 0.5 mg/kg × 2 | $-1.4\%$ $P = 0.005$ | $-12\%$ $p = 0.5$ | $-5\%$ NS | $+26\%$ (NS) $p = 0.088$ | $-18\%$ (NS) | 0 | unchanged |
| 1.0 mg/kg × 2 | $-1.9\%$ $p = 0.005$ | $-20\%$ $p = 0.2$ | $+10\%$ NS | $+41\%$ $p = 0.064$ | $-38\%$ | $-8\%$ (NS) | unchanged |
| 2.5 mg/kg × 2 | $-3.6\%$ $p = 0.005$ | $-41\%$ $p = 0.005$ | $-10\%$ NS | $+59\%$ $p = 0.025$ | $-50\%$ $p = 0.01$ | $-34\%$ $p = 0.025$ | unchanged |

N

1. An ethanolamine benzoate compound selected from those of formula I:

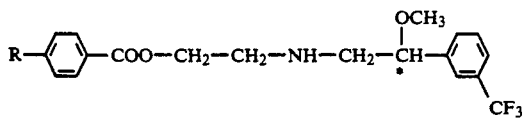

in which:
R represents:
 hydrogen, or
 a group of formula:

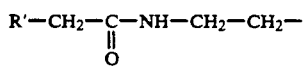

in which R' represents:
a) a radical of formula:

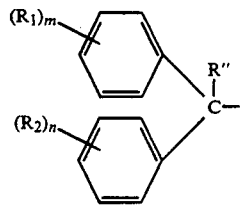

in which:
R" represents hydrogen or straight-chain or branched alkyl containing 1 to 5 carbon atoms inclusive,
$R_1$ and $R_2$, which are the same or different, each represents hydrogen or straight-chain or branched alkyl or alkoxy each having 1 to 5 carbon atoms inclusive, and m and n are the same or different and each represents 1, 2 or 3;
b) a fluorenyl radical of formula:

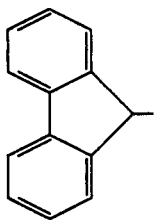

in the racemic form or in the form of an enantiomer thereof, and
physiologically-tolerable acid addition salts thereof.

2. A compound of claim 1 which is:
1-2-[(β-methoxy-β-meta-trifluoromethylphenyl)ethylamino]ethyl para-[2-(α-fluoren-9-ylacetylamino)ethyl]benzoate hydrochloride.

3. A compound of claim 1 which is:
d-2-[(β-methoxy-β-meta-trifluoromethylphenyl)ethylamino]ethyl para-[2-(α-fluoren-9-ylacetylamino)ethyl]benzoate hydrochloride.

4. A compound of claim 1 which is:
dl-2-[(β-methoxy-β-meta-trifluoromethylphenyl)ethylamino]ethyl para-[2-(α-fluoren-9-ylacetylamino)ethyl]-benzoate hydrochloride.

5. A compound of claim 1 which is:
1-2-[(β-methoxy-β-meta-trifluoromethylphenyl)ethylamino]ethyl para-[2-(benzhydrylacetylamino)ethyl]benzoate hydrochloride.

6. A compound of claim 1 which is:
dl-2-[(β-methoxy-β-meta-trifluoromethylphenyl)ethylamino]ethyl benzoate hydrochloride.

7. A compound of claim 1 which is: 1-2-[(β-methoxy-β-meta-trifluoromethylphenyl)ethylamino]ethyl benzoate hydrochloride.

8. A compound of claim 1 which is:
d-2-[(b-methoxy-β-meta-trifluoromethylphenyl)ethylamino]ethyl benzoate hydrochloride.

9. A pharmaceutical composition useful for regulating glucide and lipid metabolism comprising as active ingredient an amount of a compound according to claim 1 effective for said purpose together with a pharmaceutically-acceptable excipient.

10. A method for treating a mammal afflicted with an insulin-resistance state, comprising the step of administering to the said mammal an amount of an ethanolamine benzoate compound selected from those of formula I:

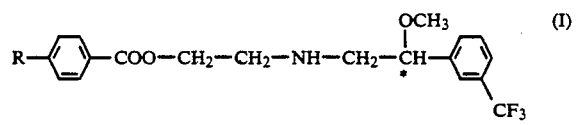

in which:
R represents:
 hydrogen, or
 a group of formula:

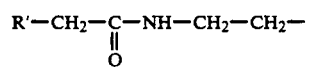

in which R' represents:
 a fluorenyl radical of formula:

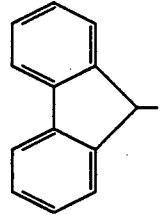

in the racemic form or in the form of an enantiomer thereof, and physiologically-tolerable acid addition salts thereof, which is effective for alleviation of the said condition.

* * * * *

UNITED STATES PATENT AND TRADEMARK OFFICE
CERTIFICATE OF CORRECTION

PATENT NO. : 5,266,718

DATED : Nov. 30, 1993

INVENTOR(S) : Michel Wierzbicki, Pierre Hugon, Jacques Duhault, Francoise Lacour, Michelle Boulanger It is certified that error appears in the above-identified patent and that said Letters Patent is hereby corrected as shown below:

Column 2, line 51; "compound for-" should read -- compound of for- --.
Column 3, line 17; "laevoratatory" should read -- levoratatory --.
Column 8, line 3; delete "J".
Column 12, line 30; "affected" should read -- effected --.
Column 14, line 10; move the "e" at the end of line 10 to the beginning of line 11 and insert before "thylamino".
Column 14, line 37; move the closing parenthesis ")" from the beginning of line 37 to the end of line 36 and insert before the hyphen.
Column 15, line 4; move the closing parenthesis ")" from the beginning of line 4 to the end of line 3 and insert before the hyphen.
Column 17, line 13; move the closing parenthesis ")" from the beginning of line 13 to the end of line 12 and insert before the hyphen.

Column 19, line 57; "desappearance" should read -- disappearance --.
Column 20, TABLE Ia, in the table, 2nd column, 4th listing under the heading; "-6% p<0.01" should read -- -6% p>0.001 --.
Column 21, TABLE II, heading, fourth column, line 1; "Glycermia" should read -- Glyycemia --.
Column 22, TABLE IV, in the table, column 2, lines 26, 27; under animal" insert -- treated --.

UNITED STATES PATENT AND TRADEMARK OFFICE
CERTIFICATE OF CORRECTION

PATENT NO. : 5,266,718

DATED : Nov. 30, 1993

INVENTOR(S) : Michel Wierzbicki, Pierre Hugon, Jacques Duhault,
Francoise Lacour, Michelle Boulanger It is certified that error appears in the above-identified patent and that said Letters Patent is hereby corrected as shown below:

Column 23, line 38; insert -- or -- before "b)". (PA, P1)
Column 23, line 55; underline "1" at the head of the line.
Column 23, line 55; move the "e" at the end of line 55 to the beginning of line 56 and insert before "thylamino".
Column 23, line 59; underline "d" at the head of the line.
Column 23, line 59; move the "e" at the end of line 59 to the beginning of line 60 and insert before "thylamino".
Column 24, line 2; underline "d1" at the head of the line.
Column 24, line 6; underline "1" at the head of the line.
Column 24, line 10; underline "d1" at the head of the line.
Column 24, line 12; underline "1" after "is:".
Column 24, line 16, underline "d" at the head of the line.

Signed and Sealed this

Twenty-sixth Day of July, 1994

*Attest:*

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,266,718
DATED : Nov. 30, 1993
INVENTOR(S) : Michel Wierzbicki et al It is certified that error appears in the above-indentified patent and that said Letters Patent is hereby corrected as shown below:

Column 19, line 56; "for the determining the" should read
-- for determining the --.

Signed and Sealed this

Eleventh Day of October, 1994

Attest:

BRUCE LEHMAN

*Attesting Officer*  *Commissioner of Patents and Trademarks*